United States Patent [19]

Teulon

[11] Patent Number: 4,786,642
[45] Date of Patent: * Nov. 22, 1988

[54] PHENYLNAPHTHYRIDINES CONTAINING A METHYL SUBSTITUENT IN THE 3-POSITION USEFUL IN THE TREATMENT OF ULCERS

[75] Inventor: Jean-Marie Teulon, La Celle Saint Cloud, France

[73] Assignee: Societe Anonyme: Carpibem, Rueil Malmaison, France

[*] Notice: The portion of the term of this patent subsequent to Nov. 11, 2003 has been disclaimed.

[21] Appl. No.: 315

[22] Filed: Jan. 5, 1987

[30] Foreign Application Priority Data

Jan. 6, 1986 [FR] France ................................ 8600102
Jan. 6, 1986 [FR] France ................................ 8600104

[51] Int. Cl.$^4$ .................. A61K 31/435; C07D 471/04
[52] U.S. Cl. ....................................... 514/300; 546/122
[58] Field of Search ........................ 546/122; 514/300

[56] References Cited

U.S. PATENT DOCUMENTS

4,622,328 11/1986 Teulon ................................ 546/122

FOREIGN PATENT DOCUMENTS

2567520 1/1986 France.

OTHER PUBLICATIONS

Chem. abstracts 105, 208847a (1986).

Primary Examiner—Mary C. Lee
Assistant Examiner—Bernard I. Dentz
Attorney, Agent, or Firm—Scully, Scott, Murphy and Presser

[57] ABSTRACT

The present invention relates to the compounds corresponding to the formula:

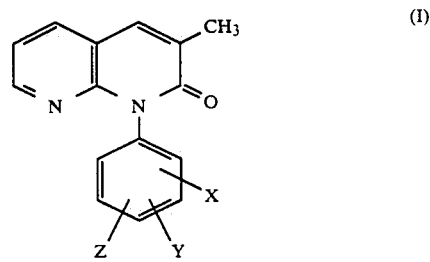

in which:
X, Y and Z are selected from the following combinations:
(a) Y=Z=H and X is m-CH$_3$, m,p-Cl, m-SCH$_3$, m,o,p-F, m,p-CN, CONH$_2$, m-CH$_2$CN or p-OH,
(b) Z=H and X and Y are fluorine, more particularly 2,5 and 2,4,
(c) Z=H, X=m-CN and Y is p-Cl or p-F, and
(d) X=Y=X=OCH$_3$ in the m,p,m positions, and to drugs in which at least one of the said compounds is present.

4 Claims, No Drawings

PHENYLNAPHTHYRIDINES CONTAINING A METHYL SUBSTITUENT IN THE 3-POSITION USEFUL IN THE TREATMENT OF ULCERS

The present invention relates to the phenylnaphthyridines of the formula (I). It also relates to the process for the preparation of the said products and their applications, especially in therapy.

The novel compounds according to the invention are selected from the group comprising the compounds of the general formula (I):

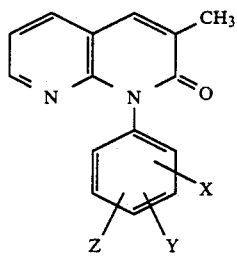

(I)

in which:

X, Y and Z are selected from the following combinations:
(a) $Z=Y=H$ and X is m-$CH_3$, m,p-Cl, m-$SCH_3$, m,o,p-F, m,p-CN, m-$CONH_2$, m-$CH_2$-CN or p-OH,
(b) $Z=H$ and Y and X are F, more particularly in the 2,5, 2,4 or 2,6 positions,
(c) $Z=H$, $X=$m-CN and Y is p-Cl or p-F, and
(d) $Z=X=Y=OCH_3$ in the m-p-m positions.

The Applicant Company has already described products belonging to the same family in French Patent Application no. 2.567.520; now, however, it has unexpectedly discovered that certain specific products belonging to the said family have improved ulcer-inhibiting properties and/or a better therapeutic index than those products belonging to the same family which were described and exemplified in the said Application.

Thus, for example, when the aromatic nucleus contains only one substituent, this substituent must be located in the meta position if it is $CH_3$, $SCH_3$, CN, $CH_2CN$ or $CONH_2$, it can be in the meta or para position if it is Cl, and it can be located in the meta, ortho or para position if it is F.

Thus, for example, it is advantageous for both the substituents on the aromatic nucleus to be F; in this case, the three combinations 2,6, 2,5 and 2,4 are possible, but the 2,5 and 2,4 positions are preferable. The combination 3-CN,4-halogen (F or Cl) is also particularly desirable.

The compounds of the formula (I) according to the invention can be synthesized by one of the following methods:
a Reformatsky reaction followed by dehydration,
a Wittig reaction followed by cyclization,
a Perkin reaction or
a Claisen reaction on an aldehyde of the formula (II):

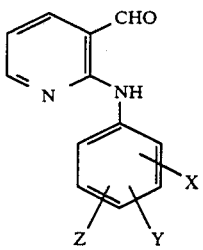

(II)

In the formula (II), X, Y and Z are defined as above.

In general, the aldehydes of the formula (II) can be obtained by the oxidation of an alcohol of the formula (III) with a mild oxidizing agent such as $MnO_2$, in an organic solvent such as methylene chloride or chloroform, at a temperature of between 20° and 50° C.

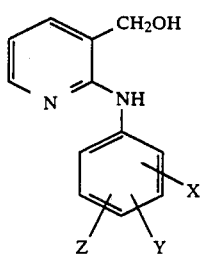

(III)

In the formula (III), X, Y and Z are defined as above.

The alcohols of the formula (III) are obtained by the classic reduction, for example with lithium aluminum hydride in an organic solvent such as tetrahydrofuran, of an acid or one of its esters of the formula (IV). In the case where the phenyl nucleus carries a substituent which is sensitive to certain reducing agents, such as a nitrile substituent, the reducing agent for reducing the ester will be chosen so as not to affect this substituent, an example being lithium borohydride prepared "in situ" from potassium borohydride and lithium chloride.

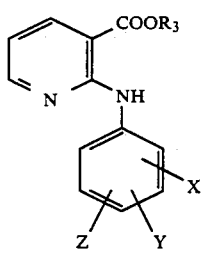

(IV)

In the formula (IV), X, Y and Z are defined as above. $R_3$ is the hydrogen atom or an alkyl.

On an industrial scale, the preferred process for synthesizing the products of the formula (I) consists in using the known Perkin reaction, whereby an aldehyde of the formula (II) is reacted with an anhydride of the formula:

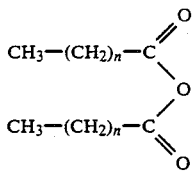

in the presence of the sodium salt of the corresponding acid.

The reaction can be carried out without a solvent or in a solvent such as N-methylpyrrolidone, at a temperature of about 100° to 200° C.

In the precise case where n=1, the reagents will be propionic anhydride and sodium propionate.

Another process which is advantageous on an industrial scale consists in using the known Claisen reaction, whereby an aldehyde of the formula (II) is reacted with acid esters of the formula:

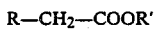

R—CH₂—COOR'

(in the present case R=CH₃, R' being an alkyl) in the presence of a sodium or potassium alcoholate, sodium hydride or sodium metal. For example, ethyl propionate and sodium ethylate will be used.

The products in which X, Y or Z is an amide are obtained by conversion of the corresponding products in which X, Y or Z possesses a nitrile functional group by means of known processes, for example by reaction with an acid.

The products in which X, Y or Z is a hydroxyl are obtained by conversion of the corresponding products in which X, Y or Z is an alkoxy by means of known processes, for example by reaction with pyridine hydrochloride or hydrobromic acid.

According to the invention, therapeutic compositions are proposed which are useful in particular for the treatment of gastrointestinal ulcers, the said compositions containing at least one compound of the formula (I) in association with an acceptable excipient.

Further characteristics and advantages of the invention will be understood more clearly from the following description of a few preparative examples which in no way imply a limitation but are given by way of illustration.

Table I below shows the structural formulae of some of the products.

EXAMPLE 1

2-(3-Methylphenyl)amino-3-hydroxymethylpyridine

Formula III: X=3-CH₃; Y=Z=H

A solution of 37.5 g of 2-(3-methylphenyl)aminonicotinic acid in 140 ml of anhydrous tetrahydrofuran is added dropwise to a suspension of 9.6 g of lithium aluminum hydride in 230 ml of anhydrous ether. After the addition has ended, the reaction mixture is stirred for 3 h at room temperature. After cooling, the excess hydride is destroyed by adding ethyl acetate and then a saturated aqueous solution of sodium sulfate. The precipitate formed is filtered off and washed with ether. The combined filtrates are evaporated in vacuo and 34.5 g of 2-(3-methylphenyl)amino-3-hydroxymethylpyridine are recovered in the form of an oil, which is used in the crude state in the next step.

The following derivatives are prepared by this method:

2-(3-chlorophenyl)amino-3-hydroxymethylpyridine
Formula III: X=3-Cl; Y=Z=H
Crystals; m.p.=114°-5° C.; yield: 94%

2-(3-methylthiophenyl)amino-3-hydroxymethylpyridine
Formula III: X=3-SCH₃; Y=Z=H
Oil; yield: 95%

2-(2,4-difluorophenyl)amino-3-hydroxymethylpyridine
Formula III: X=2-F; Y=4-F; Z=H
Oil; yield: 93%

2-(3-fluorophenyl)amino-3-hydroxymethylpyridine
Formula III: X=3-F; Y=Z=H
Crystals; m.p.=77°-8° C.; yield: 95%

2-(4-fluorophenyl)amino-3-hydroxymethylpyridine
Formula III: X=4-F; Y=Z=H
Crystals; m.p.=89°-90° C.; yield: 88%

2-(2-fluorophenyl)amino-3-hydroxymethylpyridine
Formula III: X=2-F; Y=Z=H
Crystals; m.p.=96°-8° C.; yield: 95%

2-(2,5-difluorophenyl)amino-3-hydroxymethylpyridine
Formula III: X=2-F; Y=5-F; Z=H
Crystals; m.p.=71°-4° C.; yield: 98%

2-(2,6-difluorophenyl)amino-3-hydroxymethylpyridine
Formula III: X=2-F; Y=6-F; Z=H
Crystals; m.p.=115° C.; yield: 90%

2-(4-chlorophenyl)amino-3-hydroxymethylpyridine
Formula III: X=4-Cl; Y=Z=H
Crystals; m.p.=124°-126° C.; yield: 95%

2-(4-methoxyphenyl)amino-3-hydroxymethylpyridine
Formula III: X=4-OCH₃; Y=Z=H
Crystals; m.p.=95°-6° C.; yield: 95%

2-(3,4,5-trimethoxyphenyl)amino-3-hydroxymethylpyridine
Formula III: X=3-OCH₃; Y=4-OCH₃; Z=5-OCH₃
Crystals; m.p.=127° C.; yield: 95%

EXAMPLE 2

2-(3-Cyanophenyl)amino-3-hydroxymethylpyridine

Formula III: X=3-CN; Y=Z=H 8 g of lithium chloride are added in small amounts, with stirring, to a solution of 39.3 g of methyl 2-(3-cyanophenyl)aminonicotinate in 600 ml of tetrahydrofuran containing 10 g of potassium borohydride. After the addition has ended, the mixture is heated under reflux for 4 h and then concentrated in vacuo. After water and ice have been added to the resulting residue, extraction is carried out with ether and the ether phase is washed with water and then dried over sodium sulfate. After evaporation of the ether, 31.6 g of 2-(3-cyanophenyl)amino-3-hydroxymethylpyridine are obtained in the form of crystals melting at 126° C.

The following derivatives are prepared by this process:

2-(4-cyanophenyl)amino-3-hydroxymethylpyridine
Formula III: X=4-CN; Y=Z=H
Crystals; m.p.=142° C.; yield: 93%

2-(3-cyanomethylphenyl)amino-3-hydroxymethylpyridine
Formula III: X=3-CH₂CN; Y=Z=H
Oil; yield: 35%

2-(3-cyano-4-chlorophenyl)amino-3-hydroxymethylpyridine
Formula III: X=3-CN; Y=4-Cl; Z=H
Crystals; m.p.=147° C.; yield: 90%

2-(3-cyano-4-fluorophenyl)amino-3-hydroxymethyl-
pyridine
Formula III: X=3-CN; Y=4-F; Z=H
Crystals; m.p.=126° C.; yield: 90%

EXAMPLE 3

2-(3-Methylphenyl)aminonicotinaldehyde

Formula II: X=3-CH$_3$; Y=Z=H 163 g of MnO$_2$ are added in small portions to a solution of 34.5 g of 2-(3-methylphenyl)amino-3-hydroxymethylpyridine, prepared in Example 1, in 550 ml of chloroform. After the addition has ended, the mixture is stirred at room temperature for 6 h.

The reaction medium is then filtered on celite and the filtrate is evaporated to dryness. The crystals thus obtained are recrystallized from isopropyl ether. 27 g of 2-(3-methylphenyl)aminonicotinaldehyde are thus recovered in the form of crystals melting at 95°-7° C.

The following derivatives are prepared by this method:

2-(3-chlorophenyl)aminonicotinaldehyde
Formula II: X=3-Cl; Y=Z=H
Crystals; m.p.=99°-100° C.; yield: 78%
2-(3-methylthiophenyl)aminonicotinaldehyde
Formula II: X=3-SCH$_3$; Y=Z=H
Crystals; m.p.=63°-4° C.; yield: 70%
2-(2,4-difluorophenyl)aminonicotinaldehyde
Formula II: X=2-F; Y=4-F; Z=H
Crystals (isopropanol); m.p.=135°-7° C.; yield: 75%
2-(3-fluorophenyl)aminonicotinaldehyde
Formula II: X=3-F; Y=Z=H
Crystals; m.p.=70°-72° C.; yield: 78%
2-(4-fluorophenyl)aminonicotinaldehyde
Formula II: X=4-F; Y=Z=H
Crystals; m.p.=67°-68° C.; yield: 71%
2-(2-fluorophenyl)aminonicotinaldehyde
Formula II: X=2-F; Y=Z=H
Crystals; m.p.=93°-94° C.; yield: 70%
2-(2,5-difluorophenyl)aminonicotinaldehyde
Formula II: X=2-F; Y=5-F; Z=H
Crystals (isopropanol); m.p.=129°-130° C.; yield: 76%
2-(2,6-difluorophenyl)aminonicotinaldehyde
Formula II: X=2-F; Y=6-F; Z=H
Crystals; m.p.=106° C.; yield: 93%
2-(3-cyanophenyl)aminonicotinaldehyde
Formula II: X=3-CN; Y=Z=H
Crystals (acetonitrile); m.p.=153°-154° C.; yield: 60%
2-(4-cyanophenyl)aminonicotinaldehyde
Formula II: X=4-CN; Y=Z=H
Crystals; m.p.=166° C.; yield: 93%
2-(3-cyanomethylphenyl)aminonicotinaldehyde
Formula II: X=3-CH$_2$CN; Y=Z=H
Crystals; m.p.=50° C.; yield: 92%
2-(3-cyano-4-chlorophenyl)aminonicotinaldehyde
Formula II: X=3-CN; Y=4-Cl; Z=H
Crystals (acetonitrile); m.p.=203° C.; yield: 60%
2-(3-cyano-4-fluorophenyl)aminonicotinaldehyde
Formula II: X=3-CN; Y=4-F; Z=H
Crystals (acetonitrile); m.p.=193° C.; yield: 80%
2-(4-chlorophenyl)aminonicotinaldehyde
Formula II: X=4-Cl; Y=Z=H
Crystals (isopropyl acetate); m.p.=101°-102° C.; yield: 60%
2-(3,4,5-trimethoxyphenyl)aminonicotinaldehyde
Formula II: X=3-OCH$_3$; Y=4-OCH$_3$; Z=5-OCH$_3$
Crystals; m.p.=104° C.; yield: 25%
2-(4-methoxyphenyl)aminonicotinaldehyde
Formula II: X=4-OCH$_3$; Y=Z=H
Crystals; m.p.=82°-84° C.; yield: 50%

EXAMPLE 4

1-(3-Methylphenyl)-1,2-dihydro-2-oxo-3-methyl-1,8-naphthyridine

Formula I: X=3-CH$_3$; Y=Z=H

A mixture of 10 g of 2-(3-methylphenyl)aminonicotinaldehyde, synthesized in Example 3, 6.2 g of sodium propionate and 12 ml of propionic anhydride is heated under reflux for 1 h 15 min.

The reaction mixture is then cooled, 100 ml of water are added and the resulting mixture is stirred for 30 minutes at room temperature. Extraction is carried out with methylene chloride and the organic phase is washed with water, with a 10% solution of sodium hydroxide and then again with water, dried over sodium sulfate and concentrated in vacuo. The residue obtained crystallizes. After recrystallization from isopropanol, 4.8 g of 1-(3-methylphenyl)-1,2-dihydro-2-oxo-3-methyl-1,8-naphthyridine are obtained in the form of crystals melting at 182°-3° C.

The following derivatives were prepared by this method:

EXAMPLE 5

1-(3-Chlorophenyl)-1,2-dihydro-2-oxo-3-methyl-1,8-naphthyridine

Formula I: X=3-Cl; Y=Z=H
Crystals (acetonitrile); m.p.=205°-6° C.; yield: 48%

EXAMPLE 6

1-(3-Methylthiophenyl)-1,2-dihydro-2-oxo-3-methyl-1,8-naphthyridine

Formula I: X=3-SCH$_3$; Y=Z=H
Crystals (methanol); m.p.=184°-5° C.; yield: 42%

EXAMPLE 7

1-(2,4-Difluorophenyl)-1,2-dihydro-2-oxo-3-methyl-1,8-naphthyridine

Formula I: X=2-F; Y=4-F; Z=H
Crystals (isopropanol); m.p.=188°-9° C.; yield: 49%

EXAMPLE 8

1-(3-Fluorophenyl)-1,2-dihydro-2-oxo-3-methyl-1,8-naphthyridine

Formula I: X=3-F; Y=Z=H
Crystals (dimethylformamide); m.p.=240°-1° C.; yield: 42%

EXAMPLE 9

1-(4-Fluorophenyl)-1,2-dihydro-2-oxo-3-methyl-1,8-naphthyridine

Formula I: X=4-F; Y=Z=H
Crystals (dimethylformamide); m.p.=248°-9° C.; yield: 50%

EXAMPLE 10

1-(2-Fluorophenyl)-1,2-dihydro-2-oxo-3-methyl-1,8-naphthyridine

Formula I: X=2-F; Y=Z=H
Crystals (isopropanol); m.p.=161°-3° C.; yield: 40%

EXAMPLE 11

1-(2,5-Difluorophenyl)-1,2-dihydro-2-oxo-3-methyl-1,8-naphthyridine

Formula I: X=2-F; Y=5-F; Z=H
Crystals (isopropanol); m.p.=143°-4° C.; yield: 52%

EXAMPLE 12

1-(2,6-Difluorophenyl)-1,2-dihydro-2-oxo-3-methyl-1,8-naphthyridine

Formula I: X=2-F; Y=6-F; Z=H
Crystals (ethanol); m.p.=212°-3° C.; yield: 52%

EXAMPLE 13

1-(3-Cyanophenyl)-1,2-dihydro-2-oxo-3-methyl-1,8-naphthyridine

Formula I: X=3-CN; Y=Z=H
Crystals (dimethylformamide); m.p.=266°-267° C.; yield: 70%

EXAMPLE 14

1-(4-Cyanophenyl)-1,2-dihydro-2-oxo-3-methyl-1,8-naphthyridine

Formula I: X=4-CN; Y=Z=H
Crystals (dimethylformamide); m.p.=265°-267° C.; yield: 42%

EXAMPLE 15

1-(3-Cyanomethylphenyl)-1,2-dihydro-2-oxo-3-methyl-1,8-naphthyridine

Formula I: X=3-CH$_2$CN; Y=Z=H
Crystals (filtration on silica gel, eluent: methylene chloride/acetone 98/2); m.p.=174°-176° C.; yield: 15%

EXAMPLE 16

1-(3-Cyano-4-chlorophenyl)-1,2-dihydro-2-oxo-3-methyl-1,8-naphthyridine

Formula I: X=3-CN; Y=4-Cl; Z=H
Crystals (acetonitrile); m.p.=244°-5° C.; yield: 55%

EXAMPLE 17

1-(3-Cyano-4-fluorophenyl)-1,2-dihydro-2-oxo-3-methyl-1,8-naphthyridine

Formula I: X=3-CN; Y=4-F; Z=H
Crystals (acetonitrile); m.p.=234° C.; yield: 57.5%

EXAMPLE 18

1-(4-Chlorophenyl)-1,2-dihydro-2-oxo-3-methyl-1,8-naphthyridine

Formula I: X=4-Cl; Y=Z=H
Crystals (acetonitrile); m.p.=239°-240° C.; yield: 55%

EXAMPLE 19

1-(3,4,5-Trimethoxyphenyl)-1,2-dihydro-2-oxo-3-methyl-1,8-naphthyridine

Formula I: X=3-OCH$_3$; Y=4-OCH$_3$; Z=5-OCH$_3$
Crystals (acetonitrile); m.p.=244°-5° C.; yield: 20%

EXAMPLE 20

1-(4-Methoxyphenyl)-1,2-dihydro-2-oxo-3-methyl-1,8-naphthyridine

Formula I: X=4-OCH$_3$; Y=Z=H
Crystals (dimethylformamide); m.p.=235°-6° C.; yield: 51%

EXAMPLE 21

1-(3-Cyanophenyl)-1,2-dihydro-2-oxo-3-methyl-1,8-naphthyridine

Formula I: X=3-CN; Y=Z=H

A solution of 10 g of 2-(3-cyanophenyl)aminonicotinaldehyde, prepared in Example 3, 20 ml of ethyl propionate and 20 ml of ethanol containing 0.054 mol of sodium ethylate (prepared by adding 1.25 g of sodium to 20 ml of ethanol) is stirred at room temperature for 4 h.

The precipitate formed is filtered off, washed with water and dried. After recrystallization from dimethylformamide, 5.3 g of 1-(3-cyanophenyl)-1,2-dihydro-2-oxo-3-methyl-1,8-naphthyridine are recovered in the form of crystals melting at 266°-267° C.

EXAMPLE 22

1-(3-Carbamoylphenyl)-1,2-dihydro-2-oxo-3-methyl-1,8-naphthyridine

Formula I: X=3-CONH$_2$; Y=Z=H 3.5 g of 1-(3-cyanophenyl)-1,2-dihydro-2-oxo-3-methyl-1,8-naphthyridine, prepared in Examples 13 and 21, are added in small portions, with stirring, to 10 ml of concentrated sulfuric acid. After stirring for 24 h at room temperature, 100 ml of water are added and the reaction mixture is rendered basic with an aqueous solution of ammonia. The crystals formed are filtered off, washed carefully with water and dried. After recrystallization from dimethylformamide, 2.3 g of 1-(3-carbamoylphenyl)-1,2-dihydro-2-oxo-3-methyl-1,8-naphthyridine are obtained in the form of crystals melting at 293°-295° C.

EXAMPLE 23

1-(4-Hydroxyphenyl)-1,2-dihydro-2-oxo-3-methyl-1,8-naphthyridine

Formula I: X=4-OH; Y=Z=H 8.7 g of 1-(4-methoxyphenyl)-1,2-dihydro-2-oxo-3-methyl-1,8-naphthyridine, prepared in Example 20, are heated under reflux in 300 ml of 48% hydrobromic acid for 2 h.

The reaction mixture is then cooled, water and ice are added and the resulting mixture is then neutralized with a solution of sodium bicarbonate. The crystals formed are filtered off, washed with water and dried. After recrystallization from an acetonitrile/dimethylformamide mixture, 6.3 g of 1-(4-hydroxyphenyl)-1,2-dihydro-2-oxo-3-methyl-1,8-naphthyridine are recovered in the form of crystals melting at 308° C.

TABLE I 5145-21

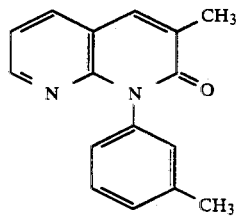

Example 4

TABLE I-continued
| | | |
|---|---|---|
| 5145-22 | 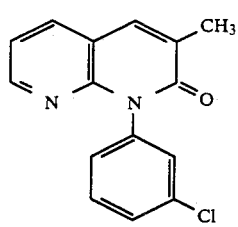 | Example 5 |
| 5145-28 | 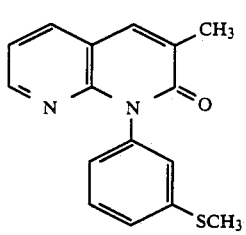 | Example 6 |
| 5145-29 | 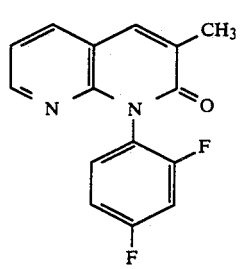 | Example 7 |
| 5145-30 | 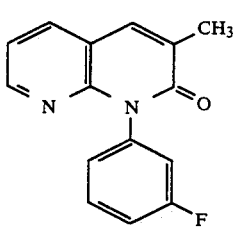 | Example 8 |
| 5145-31 | 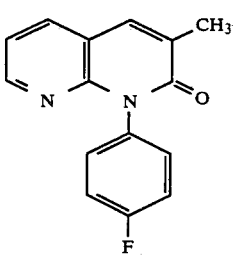 | Example 9 |
| 5145-32 | 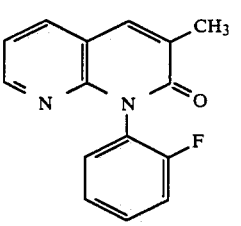 | Example 10 |
| 5145-34 | 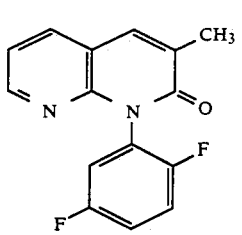 | Example 11 |
| 5145-68 | 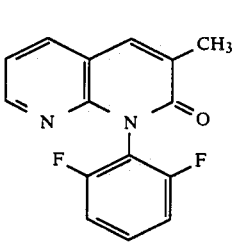 | Example 12 |
| 5145-17 | 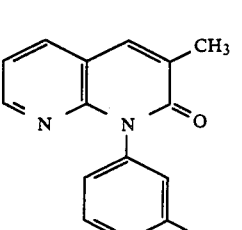 | Example 13 |
| 5145-37 | 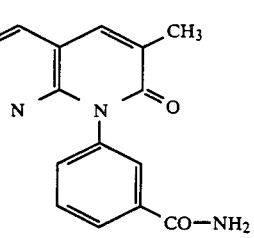 | Example 22 |
| 5145-69 | 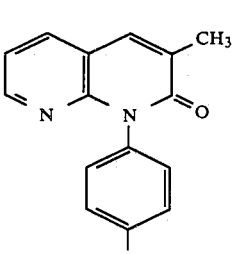 | Example 14 |
| 5145-75 | 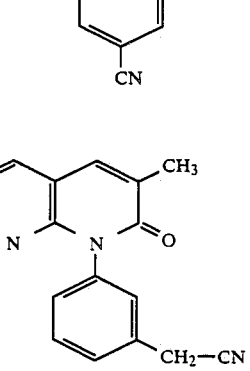 | Example 15 |

TABLE I-continued

| No. | Structure | Example |
|---|---|---|
| 5145-98 | 3-methyl-1-(4-chloro-3-cyanophenyl)-1,8-naphthyridin-2(1H)-one | Example 16 |
| 5145-104 | 3-methyl-1-(4-fluoro-3-cyanophenyl)-1,8-naphthyridin-2(1H)-one | Example 17 |
| 5145-120 | 3-methyl-1-(4-chlorophenyl)-1,8-naphthyridin-2(1H)-one | Example 18 |
| 5145-138 | 3-methyl-1-(3,4,5-trimethoxyphenyl)-1,8-naphthyridin-2(1H)-one | Example 19 |
| 5145-150 | 3-methyl-1-(4-hydroxyphenyl)-1,8-naphthyridin-2(1H)-one | Example 23 |

PHARMACOLOGY

Ulcer-inhibiting activity

1 Method

Groups of 10 to 30 male rats of the OFA strain (originating from IFFA CREDO, France), weighing 160–180 g, are put on a water-only diet 24 hours before the oral administration of the test product.

Thirty minutes after gavage, an ulcerogenic drug or a necrogenic agent (absolute ethanol) is administered orally at doses which cause the maximum gastric ulceration in the control animals. The stomachs are then removed either 6 hours or 1 hour after the final treatment, depending on the test. The gastric lesions are then evaluated macroscopically (grading and measurement of the size of the ulcers).

2 Results

The results are expressed in the form of 50% active doses (doses resulting in a 50% inhibition of the lesions caused) determined graphically from the straight line expressing the relationship between the percentage inhibition and the dose used.

| | 50% active dose (expressed in mg · kg$^{-1}$, oral administration) | |
|---|---|---|
| | (1) Administration of an ulcerogenic drug | (2) Administration of a necrogenic agent |
| Example 5 | 0.170 | 0.017 |
| Example 8 | 0.180 | 0.020 |
| Example 9 | 0.340 | 0.035 |
| Example 13 | 0.085 | 0.010 |
| Example 17 | 0.164 | 0.024 |

(1) non-steroidal antiinflammatory agent,
(2) ethanol

Antisecretory activity

1 Method

The pylorus is ligated under ether anesthetic in groups of 5 male rats of the OFA strain (originating from IFFA CREDO, France), weighing 180–200 g.

The test product is administered subcutaneously at the moment of ligation. The animals are sacrificed 4 hours later, the gastric fluid is collected and its acidity is then titrated against 0.1 N sodium hydroxide solution at pH 4 and 7.

2 Results

The results are expressed as 50% active doses (doses resulting in a 50% inhibition of the total acid secretion) determined graphically from the straight line expressing the percentage inhibition of the total acid secretion as a function of the dose used.

| | 50% active dose (expressed in mg · kg$^{-1}$, subcutaneous administration) |
|---|---|
| Example 5 | 0.038 |
| Example 8 | 0.045 |
| Example 9 | 0.040 |
| Example 13 | 0.050 |
| Example 17 | 0.064 |

TOXICOLOGY

The first toxicological studies, performed on fasted Sprague Dawley rats after oral administration, made it possible to show that the LD$_{50}$ values for the products exemplified are greater than or equal to 300 mg·kg$^{-1}$.

CONCLUSION

The products according to the invention and their non-toxic acid addition salts described in the present Application seem to be of particular value; their ulcer-inhibiting and antisecretory activities are extremely powerful and superior to those described for the derivatives forming the subject of French Patent Application 2.567.520. They may be used in the treatment of gastroduodenal ulcers by injection or oral administration in the form of injectable ampoules, tablets or gelatin capsules containing doses of 5 to 100 mg.

What is claimed is:

1. A compound of the formula:

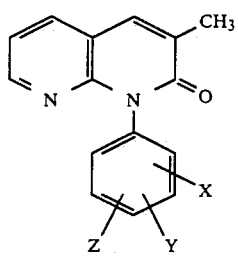
(I)

in which:

X, Y and Z are selected from the following combinations:

(a) Y=Z=H and X is m-CH₃, m-Cl, m-SCH₃, m, p-F, m-CN, m-CH₂-CN, (b) Z=H, X=2-F and Y=5-F and (c) Z=H, X=m-CH and Y is p-Cl or p-F.

2. The compound according to claim 1 which is selected from the group consisting of:

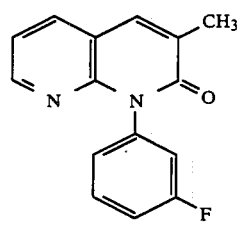

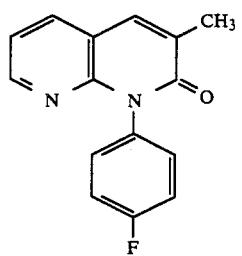

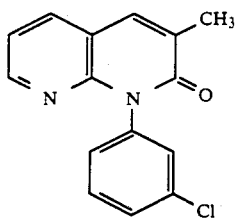

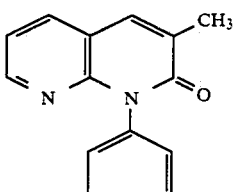

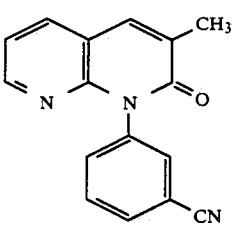

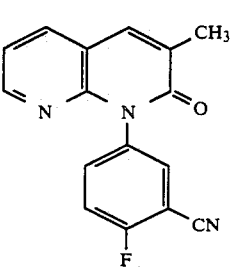

3. A pharmaceutical composition useful for the treatment of gastro-intestinal ulcer comprising an anti-ulcer effective amount of a compound according to claim 1 in association with a physiologically acceptable excipient.

4. The pharmaceutical composition as in claim 3, in dosage unit form, which contains from about 5 to 100 mg of the compound in association with a physiologically acceptable excipient.

* * * * *